United States Patent [19]

Li et al.

[11] Patent Number: 5,120,527

[45] Date of Patent: * Jun. 9, 1992

[54] PARAMAGNETIC OIL EMULSIONS AS MRI CONTRAST AGENTS

[76] Inventors: King Chuen Peter Li, 4101 East Medlock Dr., Phoenix, Ariz. 85018; Peter Gwan Pa Ang, 2932 N.W. 24th Terrace, Gainesville, Fla. 32605

[*] Notice: The portion of the term of this patent subsequent to Nov. 12, 2008 has been disclaimed.

[21] Appl. No.: 583,731

[22] Filed: Sep. 19, 1990

Related U.S. Application Data

[63] Continuation-in-part of Ser. No. 424,053, Oct. 19, 1989, Pat. No. 5,064,636.

[51] Int. Cl.$^5$ .................... G01N 31/00; G01N 24/00; A61K 31/295
[52] U.S. Cl. .......................................... 424/9; 424/4; 424/535; 436/173; 514/502; 514/836; 514/938; 514/943; 514/974; 514/975
[58] Field of Search ............... 429/9, 535, 4; 436/173; 128/653 R, 653 AF, 653 CA, 654; 514/502, 558, 560, 943, 974, 975, 938, 836

[56] References Cited

U.S. PATENT DOCUMENTS

| | | | |
|---|---|---|---|
| 3,992,555 | 11/1976 | Kovacs | 426/72 |
| 4,216,236 | 8/1980 | Mueller et al. | 426/72 |
| 4,615,879 | 10/1986 | Runge et al. | 424/9 |
| 4,675,173 | 6/1987 | Widder | 424/9 |
| 4,719,098 | 1/1988 | Weinmann et al. | 424/9 |
| 4,728,575 | 3/1988 | Gamble et al. | 428/402.2 |
| 4,731,239 | 3/1988 | Gordon | 424/9 |
| 4,827,945 | 5/1989 | Groman et al. | 128/653 R |

FOREIGN PATENT DOCUMENTS 0245019 11/1987 European Pat. Off. .

OTHER PUBLICATIONS

Clanton, Jeffrey, A., "Oral Contrast Agents", Magnetic Resonance Imaging, vol. I, Chap. 48, pp. 830-837, W. B. Saunders Company (1988).
Stark, David D. and Bradley, William G., Jr., "Gastrointestinal Contrast Agents", Magnetic Resonance Imaging, pp. 1134-1139, The C. V. Mosby Company, St. Louis, MO (1988).
Burnett, K. R., Goldstein, E. J., Wolf, G. L., Sen. S., and Mamourian, A. C., "The Oral Administration of MnCL$_2$: A Potential Alternative to IV Injection for Tissue Contrast Enhancement in Magnetic Resonance Imaging", Magnetic Resonance Imaging, vol. 2, pp. 307-314, Pergamon Press, Ltd. (1984).
Mamourian, A. C., Burnett, K. R., Goldstein, E. J., Wolf, G. L., Kressel, H. Y. and Baum, S., "Proton Relaxation Enhancement in Tissue Due to Ingested Manganese Chloride: Time Course and Dose Response in the Rat", Physiological Chemistry and Physics and Medical NMR, 16, pp. 123-128 (1984).
Wesbey, G. E., Brasch, R. C., Goldberg, H. I., and Engelstad, B. L., "Dilute Oral Iron Solutions as Gastrointestinal Contrast Agents for Magnetic Resonance Imaging: Initial Clinical Experience", Magnetic Resonance Imaging, vol. 3, pp. 57-64 (1985).
Runge, V. M., Stewart, R. G., Clanton, J. A., Jones, M. M., Lukehart, C. M. Partain, C. L., and James, A. E., Jr., "Work in Progress: Potential Oral and Intravenous Paramagnetic NMR Contrast Agents", Radiology, vol. 147, No. 3, pp. 789-791 (Jun. 1983).
Laniado, M., Kornmesser, W., Hamm, B., Clauss, W., Weinmann, H-J., and Felix, R., "MR Imaging of the Gastrointestinal Tract: Value of Gd-DTPA", Amer. Jour. of Roentgenology, 150:817-821 (Apr. 1988).
Widder, D. J., Edelman, R. R., Grief, W. L. and Monda, L., "Magnetite Albumin Suspension: A Superparamagnetic Oral MR Contrast Agent", Amer. Jour. of Roentgenology, 149:839-843 (Oct. 1987).
Hahn, P. F., Stark, D. D., Saini, S., Lewis, J. M., Wittenberg, J., and Ferrucci, J. T., "Ferrite Particles for Bowel Contrast in MR Imaging: Design Issues and Feasibility Studies", Radiology, 164, pp. 37-41 (Jul 1987).
Li, K. C. P., Tart, R. P., Storm, B., Rolfes, R., Ang, P., and Ros, P. R., "MRI Oral Constrast Agents: Comparative Study of five Potential Agents in Humans", Proceedings of the Eighth Annual Meeting of the Society of Magnetic Resonance in Medicine, Amsterdam, (Aug. 18, 1989), p. 791.
Weinreb, J. C., Maravilla, K. R., Redman, H. C., and Nunnally, R., "Improved MR Imaging of the Upper Abdomen with Glucagon and Gas", J. Comput. Assist. Tomogr., vol. 8, pp. 835-838 (1984).
Mattrey, R. F., Hajek, P. C., Gylys-Morin, V. M. Baker, L. L., Martin, J., Long, D. C., and Long, D. M., "Perfluorochemicals as Gastrointestinal Contrast Agents for MR Imaging: Preliminary Studies in Rats and Humans", Amer. Jour. of Roenigehology, 148, pp. 1259-1263 (Jun. 1987).
Mattrey, R. F., "Perfluorooctylbromide: A New Contrast Agent for CT, Sonography, and MR Imaging", Amer. Jour. of Roentgenology, 152:247-252 (Feb. 1989).

(List continued on next page.)

Primary Examiner—Richard L. Raymond
Assistant Examiner—Garry E. Hollingden
Attorney, Agent, or Firm—Speckman & Pauley

[57] ABSTRACT

A paramagnetic oil emulsion for magnetic resonance imaging composed of about 5 to about 30 volume percent oil and about 70 to about 95 volume percent aqueous-based paramagnetic agent carrier, at least one of the aqueous-based paramagnetic agent carrier and the oil having dissolved therein a magnetic resonance image contrast effective and less than a toxic amount of at least one soluble paramagnetic agent. The paramagnetic oil emulsion provides high intensity magnetic resonance signals in the gastrointestinal tract for MRI evaluation of the abdomen and pelvis, particularly in the distal bowel regions.

48 Claims, No Drawings

OTHER PUBLICATIONS

Newhouse, J. H., Brady, T. J., Gebhardt, M., Burt, C. T., Pykett, I. L., Goldman, M. R., Buonanno, F. S., Kistler, J. P., Hinshaw, W. S., and Pohost, G. M., "NMR Imaging: Preliminary Results in the Upper Extremities of Man and the Abdomen of Small Animals", *Radiology*, vol. 142, No. 1, p. 246 (Jan. 1982). (Abstract).

Paula, T. Beall, "Safe Common Agents for Improved NMR Contrast", *Physiological Chemistry and Pysics and Medical NMR, No. 16, pp. 129-135 (1984)*.

Chen, B., Gore, J. C., Zhong, J. H., McCarthy, S., Lange R. C., Helzberg, J. Young, R. S. K., and Wong, M., "Gastrointestinal MRI Contrast Enhancement by Liquid Food", *Proceedings of the 7th Annual Meeting of the Society of Magnetic Resonance in Medicine*, p. 733 (1988).

G. S. Bisset III, "Evaluation of Potential Proctical Oral Contrast Agents for Pediatric Magnetic Resonance Imaging", *Pediatric Radiology*, 20:61-66 (1989).

Raptopoulos, V., Davis, M. A., Davidoff, A., Karellas, A., Hays, D., D'Orsi, C. J., and Smith, E. H., "Fat-Density Oral Contrast Agent for Abdominal CT", *Radiology*, 164:653-656 (1987).

Raptopoulos, V., Davis, M. A., and Smith, E. H., "Imaging of the Bowel Wall: Computed Tomography and Fat Density Oral-Contrast Agent in an Animal Model", *Radiology*, 21:847-850 (1986).

Baldwin, G. N., "Computed Tomography of the Pancreas: Negative Contrast Medium", *Radiology*, 128:827-828 (1978).

Young, I. R., Clarke, G. J., Bailes, D. R., Pennock, J. M., Doyle, F. H., and Bydder, G. M., "Enhancement of Relaxation Rate with Paramagnetic Contrast Agents in NMR Imaging", *Computed Tomography*, vol. 5, No. 6, pp. 543-547 (1981).

Reynolds, J. E. F., and Prasad, A. B., "The Extra Pharmacopoeia", *Martindale*, 28th Edition, p. 875, (1982).

The United States Dispensatory, 25th Edition, J. B. Lippincott Co., pp. 568-569, (1955).

PARAMAGNETIC OIL EMULSIONS AS MRI CONTRAST AGENTS

CROSS REFERENCE TO RELATED APPLICATION

This application is a continuation-in-part of Ser. No. 07/424,053, filed Oct. 19, 1989 now U.S. Pat. No. 5,064,636 issued Nov. 12, 1991.

BACKGROUND OF THE INVENTION

1. Field of the Invention

This invention relates to magnetic resonance imaging (MRI) of the human body and to the use of paramagnetic contrast agents to improve the diagnostic usefulness of the MR images. More particularly, this invention is concerned with paramagnetic oil emulsions as MRI contrast agents and their use in MRI evaluation of the abdomen and pelvis. One important aspect of this invention is provision of a palatable oral MRI contrast agent which distributes evenly to provide effective MRI of the distal bowel to afford good diagnosis of soft tissue abnormalties.

2. Description of the Prior Art

Magnetic resonance imaging is a useful diagnostic tool due to its good tissue differentiation. The imaging is enhanced by use of paramagnetic contrast agents which affect the relaxation times T1 (spin-lattice) and T2 (spin-spin) of hydrogen atoms present in the body materials. In abdominal MRI, bowel loops and intraluminal contents can mimic pathology such as adenopathy, pancreatic or other retroperitoneal lesions. Therefore, the development of a reliable MRI contrast agent, preferably a palatable oral agent, is required before gastrointestinal MRI can assume a major role clinically.

Current review articles indicate that a problem in gastrointestinal tract MRI examinations has been stimulation of peristalsis, lack of contrast, and the lack of acceptable oral contrast agents. Particularly, magnetic contrast agents have not been developed for small bowel lumen. Clanton, Jeffrey A., "Oral Contrast Agents,"0 *Magnetic Resonance Imaging*, Vol. I, Chap. 48, pp. 830-837, W. B. Saunders Company (1988). Stark, David D. and Bradley, William G., Jr., "Gastrointestinal Contrast Agents," *Magnetic Resonance Imaging*, pp. 1134-1139, The C. V. Mosby Company, St. Louis, Mo. (1988).

In the past few years, a variety of agents have been advocated as potential oral MRI contrast agents. However, none of them satisfies all the criteria of a satisfactory agent including: uniform effect throughout the gastrointestinal tract; good patient acceptance; no side effects; and ability to mix freely with intestinal contents. The potential oral MRI contrast agents that have been proposed can be divided into four different categories.

The first group includes miscible positive agents, such as $MnCl_2$, Burnett, K. R., Goldstein, E. J., Wolf, G. L., Sen, S., and Mamourian, A. C., "The Oral Administration of $MnCl_2$: A Potential Alternative to IV Injection for Tissue Contrast Enhancement in Magnetic Resonance Imaging," *Magnetic Resonance Imaging*, Vol. 2, pp. 307-314, Pergamon Press, Ltd. (1984); Mamourian, A. C., Burnett, K. R., Goldstein, E. J., Wolf, G. L., Kressel, H. Y. and Baum, S., "Proton Relaxation Enhancement in Tissue Due to Ingested Manganese Chloride: Time Course and Dose Response in the Rat," *Physiological Chemistry and Physics and Medical NMR*, 16, pp. 123-128 (1984); dilute iron aqueous solutions such as Geritol®, ferric ammonium citrate, Wesbey, G. E., Brasch, R. C., Goldberg, H. I., and Engelstad, B. L., "Dilute Oral Iron Solutions as Gastrointestinal Contrast Agents for Magnetic Resonance Imaging: Initial Clinical Experience," *Magnetic Resonance Imaging*, Vol. 3, pp. 57-64 (1985); metal chelates, Runge, V. M., Stewart, R. G., Clanton, J. A., Jones, M. M., Lukehart, C. M., Partain, C. L., and James, A. E., Jr., "Work in Progress: Potential Oral and Intravenous Paramagnetic NMR Contrast Agents," *Radiology*, Vol. 147, No. 3, pp. 789-791 (Jun., 1983); 0.06% solution of ferric chloride, Young, I. R., Clarke, G. J., Bailes, D. R., Pennock, J. M., Doyle, F. H., and Bydder, G. M., "Enhancement of Relaxation Rate with Paramagnetic Contrast Agents in NMR Imaging", *Computed Tomography*, 5, pp. 543-546 (1981); protein and very low iron concentration to delineate soft tissue of the stomach, duodenum and jejunum, Chen, B., Gore, J. C., Zhong, J. H., McCarthy, S., Lange, R. C., Helzberg, J., Young, R. S. K., and Wong, M., "Gastrointestinal MRI Contrast Enhancement by Liquid Food", Proc. of the 7th Annual Meeting of the Society of Magnetic Resonance in Medicine, San Francisco, Calif., Aug. 20-26, pp. 733 (1988): low amounts of iron in infant formula drinks, Bisset III, G. S., "Evaluation of Potential Practical Oral Contrast Agents for Pediatric Magnetic Resonance Imaging", *Pediatric Radiology*, 20, pp. 61-66 (1989); and Gd-DTPA with mannitol, Laniado, M., Kornmesser, W., Hamm, B., Clauss, W., Weinmann, H-J., and Felix, R., "MR Imaging of the Gastrointestinal Tract: Value of Gd-DTPA," *Amer. Jour. of Roentgenology*, 150:817-821 (Apr., 1988). Oral contrast agents in aqueous solutions including osmotically active material, such as mannitol, are taught by U.S. Pat. No. 4,719,098. The disadvantages of these agents include significant dilutional effect from gastric, biliary and pancreatic secretions in the proximal small bowel resulting in failure to show effects distal to the ligament of Treitz, patient non-acceptance of metallic taste, complex absorptive process in the distal small bowel resulting in unpredictable and varying concentrations in the GI tract, and in the case of Gd-DTPA with mannitol some patients experienced diarrhea, probably due to the osmotic effect of mannitol.

The second group includes immiscible negative agents such as ferrite particles, Widder, D. J., Edelman, R. R., Grief, W. L. and Monda, L., "Magnetite Albumin Suspension: A Superparamagnetic Oral MR Contrast Agent," *Amer. Jour. of Roentgenology*, 149:839-843 (Oct., 1987); Hahn, P. F., Stark, D. D., Saini, S., Lewis, J. M., Wittenberg, J., and Ferrucci, J. T., "Ferrite Particles for Bowel Contrast in MR Imaging: Design Issues and Feasibility Studies," *Radiology*, 164, pp. 37-41 (Jul., 1987); and U.S. Pat. No. 4,731,239 which depends upon cellular metabollic processes for MRI signal enhancement. Micellular particles such as phospholipid vesicles enclosing a paramagnetic material as contract agents for NMR imaging is taught by U.S. Pat. No. 4,728,575. These vesicles are targeted to accumulate in tumor tissue after intravenous injection. Aqueous suspensions of particles of water insoluble paramagnetic compounds suitable for oral or rectal administration for gastrointestinal NMR imaging are taught by U.S. Pat. No. 4,615,879. U.S. Pat. No. 4,675,173 teaches use of encapsulated ferromagnetic contrast agents in critically sized microspheres of protein, carbohydrate or lipid biodegradable matrix for intravenous administration and segregation in the liver and spleen for magnetic resonance imaging. Superparamagnetic metal oxides coated with polysaccharides are taught to be biologically degradable and a contrast agent for MRI by U.S. Pat. No. 4,827,945. The disadvantages of this group include the fact that with high concentrations, the homogeneity of the magnetic field may be distorted and produce image artifacts. This is especially detrimental in gradient echo imaging.

The third group includes immiscible positive agents such as aqueous oil emulsions: Li, K. C. P., Tart, R. P., Storm, B., Rolfes, R., Ang, P., and Ros, P. R., "MRI Oral Contrast Agents: Comparative Study of Five Potential Agents in Humans," Proceedings of the Eighth Annual Meeting of the Society of Magnetic Resonance in Medicine, Amsterdam, Aug. 18, 1989, p. 791; European Patent Publication 0,245,019 teaches low density contrast medium of oil in water emulsion which may contain soluble salts (sodium chloride) or sugars (dextrose) to maintain homeostasis in the intestine and points out problems of unopacified bowel loops. The major disadvantage of this group is that even with very concentrated oil emulsions, the enhancement effect is not adequate when T1 weighted pulse sequences are used.

The use of oils and high lipid liquid to increase NMR contrast is known: Newhouse, J. H., Brady, T. J., Gebhardt, M., Burt, C. T., Pykett, I. L., Goldman, M. R., Buonanno, F. S., Kistler, J. P., Hinshaw, W. S. and Pohost, G. M., "NMR Imaging: Preliminary Results in the Upper Extremities of Man and the Abdomen of Small Animals", Radiology, Vol. 142, No. 1, pp. 246 (Jan. 1982) teaching use of mineral oil; Paula T. Beall, "Safe Common Agents for Improved NMR Contrast" Physiological Chemistry and Physics and Medical NMR, No. 16, pp. 129-135 (1984) teaching use of olive oil. Corn oil emulsions for use as a negative density oral contrast agent for imaging bowel wall in CAT scan is taught by Raptopoulos, V., Davis, M. A., and Smith, E. H., "Imaging of the Bowel Wall: Computed Tomography and Fat Density Oral-Contrast Agent in Animal Model", Investigational Radiology, 21, pp. 847-850 (1986) and Raptopoulos, V., Davis, M. A., Davidoff, A., Karellas, A., Hays, D., D'Orsi, C. J. and Smith, E. H., "Fat Density Oral Contrast Agent for Abdominal CT", Radiology, 164, pp. 653-656 (1987). Corn oil is taught to be a useful oral negative contrast agent for pancreas CAT scans by Baldwin, G. N., "Computed Tomography of the Pancreas: Negative Contrast Medium", Radiology, 128, pp. 827-828 (1978).

The fourth group includes immiscible negative agents such as $CO_2$ gas tablets, Weinreb, J. C., Maravilla, K. R., Redman, H. C., and Nunnally, R., "Improved MR Imaging of the Upper Abdomen with Glucagon and Gas," J. Comput. Assist., Tomog. 8, pp. 835-838 (1984), perfluorocarbons, Mattrey, R. F., Hajek, P. C., Gylys-Morin, V. M., Baker, L. L., Martin, J., Long, D. C., and Long, D. M., "Perfluorochemicals as Gastrointestinal Contrast Agents for MR Imaging: Preliminary Studies in Rats and Humans", Amer. Jour. of Roentgenology, 148, pp. 1259-1263 (Jun., 1987); Mattrey, R. F., "Perfluorooctylbromide: A New Contrast Agent for CT, Sonography, and MR Imaging," Amer. Jour. of Roentgenology, 152:247-252 (Feb., 1989), and kaolin-pectin, Li, K. C. P., Tart, R. P., Storm, B., Rolfes, R., Ang, P., and Ros, P. R., supra. This group has high potentials. However, $CO_2$ is limited to applications to the proximal GI tract. Perfluorocarbons are not FDA approved yet for clinical use and kaolin-pectin may cause severe constipation in the dosages suggested.

Iron as a dietary requirement is known: infant milk formulas containing very low amounts of iron are known from U.S. Pat. No. 4,216,236; solid fat encapsulated food particles containing ferric ammonium citrate, vitamins, minerals or mixtures thereof to provide increased dietary assimilable iron, vitamins, minerals or mixtures thereof are taught by U.S. Pat. No. 3,992,555.

SUMMARY OF THE INVENTION

This invention relates to a paramagnetic oil emulsion suitable for enteric administration wherein the emulsion comprises about 5 to about 30 volume percent oil, preferably about 15 to about 25 volume percent oil, and about 70 to about 95 volume percent, preferably about 75 to about 85 volume percent, aqueous based paramagnetic agent carrier and having therein a magnetic resonance contrast effective and less than a toxic amount of at least one paramagnetic agent. In one preferred embodiment, a water-soluble paramagnetic agent is dissolved in the aqueous based paramagnetic agent carrier. By the terminology "aqueous based or aqueous paramagnetic agent carrier" we mean to include any aqueous media in which the paramagnetic agent may be dissolved and which forms an emulsion with the oil. The aqueous based paramagnetic agent carrier is an active carrier in enhancement of even distribution of paramagnetic agent, particularly in distal bowel regions, and preferably includes nutritious materials such as milk and, for oral administration, includes flavor enhancers, such as ice cream or similar aqueous based materials to render the oil emulsion acceptable for human oral ingestion. Inclusion of an aqueous based carrier such as ice cream, in addition to flavor enhancement, provides emulsifiers for stabilization of the oil emulsion over long periods of time. Milk and ice cream aid in obtaining desired distribution of the paramagnetic agent, particularly in lower bowel regions of adults. One skilled in the art can readily ascertain the "magnetic resonance contrast effective and less than a toxic amount" of paramagnetic agent suitable for us with the paramagnetic oil emulsion of this invention, depending upon the specific paramagnetic agent used. Suitable amounts are those providing desired magnetic resonance image contrast while not inflicting any toxic or undesirable effects to the patient. We have found when using ferric ammonium citrate, a preferred paramagnetic agent, that about 0.75 to about 3 grams total dosage is required for positive enhancement throughout the small bowel of adults for gradient echo and spin echo magnetic resonance sequences. For adults, ferric ammonium citrate can be given in doses from 1 to 2 grams three or four times daily (The United States Dispensatory, 25th Edition, J. B. Lippincott Co., 1955) or up to 6 grams daily (Martindale, The Extra Pharmacopoeia, 28th Edition, The Pharmaceutical Press, London, 1982).

This invention includes a method of imaging a body cavity, such as abdomen and pelvis, of a patient by magnetic resonance after administration, preferably oral, to the patient of a magnetic resonance contrast medium as described above. Particularly, the invention includes a method for obtaining an in vivo magnetic resonance image of the abdomen and/or pelvis of a human subject by administering to the subject an effective amount of a paramagnetic oil emulsion as described above and obtaining the magnetic resonance image after a time period sufficient to allow the paramagnetic oil emulsion to pass to the desired portion of the gastrointestinal tract. The paramagnetic oil emulsion is preferably administered orally and/or rectally and effective distribution through the small intestine occurs within about 30 to about 180 minutes post oral administration, and almost immediately in the colon post rectal administration. Oral ingestion is preferably carried out over about 90 minutes prior to scanning for a good distribution of contrast agent in the small intestine. Glucagon may be administered in amounts of about 0.2 to 0.6 mg. intramuscularly immediately prior to scanning to provide good control of motion artifacts. Even distribution of the paramagnetic oil emulsion occurs through the gastrointestinal tract increasing the magnetic resonance signal intensity difference between the gastrointestinal tract and other abdominal organs or pathologic tissues without loss of anatomical detail.

The combination of oil-in-water emulsion and paramagnetic agent according to this invention, results in a synergism unobtainable by either alone, namely, even distribution and good magnetic resonance image intensification, particularly in distal bowel regions of adults. Preferred embodiments provide a palatable oral dosage which is high in patient acceptability and diagnostic reliability.

DESCRIPTION OF PREFERRED EMBODIMENTS

The paramagnetic oil emulsion of this invention may be formulated using about 5 to about 30, preferably about 15 to about 25, volume percent, based upon the product paramagnetic oil emulsion, of any physiologically compatible oil. We have found that emulsions, wherein the oil comprises predominantly over 50 and up to 100 volume percent vegetable oil, function satisfactorily. In preferred embodiments, the vegetable oil may be selected from corn, olive, peanut, soybean, and mixtures of such oils. Corn oil is a particularly preferred oil. We have found that for most commonly used magnetic resonance spin echo and gradient echo pulse sequences the intensity of the corn oil emulsions peaks at about 15 to about 25 volume percent corn oil. We have found, using corn oil, that paramagnetic oil emulsions comprising less than about 5 volume percent oil, based upon the total paramagnetic oil emulsion, result in patchy distribution in the small bowel, especially in the distal small bowel of an adult. Using above about 10 volume percent corn oil results in even distribution in the small bowel and we have found that about 20 volume percent corn oil is acceptable in taste while providing consistent even distribution in the small bowel. We have also observed that none of the unmixed components of the paramagnetic oil emulsions of this invention has a high signal intensity with all pulse sequences: SPIN ECHO 550/22, SPIN ECHO 2000/90, FLASH 40/18/10°, FLASH 40/18/30°, FLASH 40/18/50°, FLASH 40/18/70°, and FLASH 40/18/90°.

The aqueous paramagnetic agent carrier portion of the paramagnetic oil emulsion of this invention may be formulated using about 70 to about 95, preferably about 75 to about 85, volume percent, based upon the product paramagnetic oil emulsion, and may comprise any physiologically compatible aqueous solution. It is preferred that the aqueous paramagnetic agent carrier be nutritious and of desirable taste. In preferred embodiments, the aqueous paramagnetic agent carrier comprises milk and a flavor enhancer, such as ice cream or like flavoring components. We have found milk, or chemically similar, aqueous based material to aid in the even distribution of a water soluble paramagnetic agent, particularly in the small bowel region. We have found that where the aqueous paramagnetic carrier comprises about 20 to about 60 volume percent milk and about 20 to about 40 volume percent ice cream, based upon the total of the oil emulsion, the taste of the paramagnetic oil emulsion is very acceptable to human patients. Other similar flavor enhancers may be used. Ice cream is a particularly preferred flavor enhancer since it also contains emulsifiers which provide very long-time stability to the paramagnetic oil emulsion and enhances distribution of the paramagnetic agent, particularly in the small bowel.

Suitable paramagnetic agents for use in this invention are solubilized in at least one phase of the oil-in-water emulsion according to this invention. The paramagnetic agent may be completely solubilized in either the aqueous or oil phase or may be present in both the aqueous and oil phases. In one preferred embodiment, water soluble paramagnetic agents are dissolved in the water phase of the paramagnetic oil emulsion of this invention. Paramagnetic agents known to the art may be used in a magnetic resonance image contrast effective and less than a toxic amount. The magnetic resonance image contrast effective an toxic amount of specific paramagnetic agents will be known to those skilled in the art, and if not, can be ascertained by routine experimentation. In preferred embodiments, the paramagnetic agent comprises an iron-based material. A particularly preferred water-soluble paramagnetic agent is ferric ammonium citrate. Many currently used well-known paramagnetic agents are suitable for use in this invention, such as ferric ammonium citrate, gadolinium-DTPA, chromium-DTPA, chromium-EDTA, manganese-DTPA, manganese-EDTA, manganese chloride, iron sulfate and mixtures thereof. We have found, using the paramagnetic oil emulsion of this invention, that the magnetic resonance signal intensity peaks with use of ferric ammonium citrate present in the form of Geritol ® at about 7.5 to about 12.5 volume percent Geritol ®, based upon the total paramagnetic oil emulsion. We have found for small bowel MRI in adults using the paramagnetic oil emulsions of this invention that the total dose of 1 gm ferric ammonium citrate (at 2 gms/l) produced good enhancement with gradient echo pulse sequences but variable enhancement in different subjects with the T1 weighted spin echo pulse sequences while the total dose of 3 gms ferric ammonium citrate (at 6 gms/l) produced good enhancement with all gradient echo and spin echo pulse sequences normally used. At a concentration of 6 gms/l, a mild metallic aftertaste was present which was easily masked by chewing gum or candy. The preferred dosage for oral administration is about 2 to about 3 gms ferric ammonium citrate at a concentration of about 4 to about 6 gms/l.

Thickening agents may be used to increase the viscosity of the paramagnetic oil emulsion of this invention to enhance distribution throughout the small bowel. Suitable thickening agents include those of the fibrous or film type, such as Metamucil, gelatin, methyl cellulose, agar, pectin and mixtures thereof. Suitably, about 2 to about 8 percent thickening agent may be used. We have found about 25 to about 60 gms Metamucil/liter oil emulsion to be suitable.

The aqueous based paramagnetic agent carrier and/or the paramagnetic agent may be provided in dehydrated dry powder form and mixed with water for formulating the paramagnetic oil emulsion. The paramagnetic oil emulsions of this invention may be formulated by mixing the oil and aqueous based paramagnetic agent carrier with the paramagnetic agent in a blender, such as a Waring blender, at high speed for about two to five minutes. The paramagnetic oil emulsions will be stable for a time period sufficient to allow administration and imaging of a body cavity of a patient by magnetic resonance after enteric administration. However, physiologically compatible emulsifiers, such as are well-known to the art, for example as included in ice cream, may be added to the mixture which is emulsified to provide long-term storage stability of the emulsion.

The paramagnetic oil emulsion according to this invention may be used for imaging a body cavity of a patient by magnetic resonance after administration to the patient of a magnetic resonance contrast medium of the above described paramagnetic oil emulsion. In preferred embodiments in vivo magnetic resonance images of the gastrointestinal tract of a human subject may be obtained by administering orally to the subject an effective amount of a paramagnetic oil emulsion, as described above, followed by obtaining the magnetic resonance image after a time period sufficient to allow the paramagnetic oil emulsion to pass to the desired portion of th gastrointestinal tract. Methods of obtaining magnetic resonance images of gastrointestinal tracts are known to those skilled in the art and preferred methods are set forth in the following specific examples.

We have found using a paramagnetic oil emulsion of this invention comprising 0.9 gm ferric ammonium citrate, 100 cc corn oil, 150 cc ice cream, and 250 cc homogenized milk that even distribution throughout the small bowel of an adult is obtained from 1 hour to 2 hours post a single oral administration to provide excellent gradient echo imaging. However, when spin echo imaging which requires longer imaging time is used, a multiple oral administration scheme is preferred, such as splitting the dosage into four or five oral administrations over a period of about 90 minutes prior to imaging. A preferred oral ingestion scheme is even proportions of the dose at 90 min., 60 min., 30 min., 15 min., and immediately prior to scanning.

We have found that motion artifacts may be significantly reduced in MRI according to this invention when an adult is additionally administered about 0.2 to about 0.6 mg glucagon prior to MR scanning, preferably about 0.3 to about 0.4 mg glucagon intramuscular immediately prior to scanning. This administration is effective, free from side effects and easy to administer.

One preferred paramagnetic oil emulsion according to this invention has the formulation in volume percent: 38% milk, 30% ice cream, 20% corn oil, 12% Geritol ®. We have found this formulation provides a safe, effective MRI contrast agent with high patient acceptance for oral administration. We have found using this formulation that the entire small bowel becomes homogeneously brighter than surroundings when imaged with all commonly utilized magnetic resonance spin echo and gradient echo pulse sequences. We have found intensity enhancement to be much stronger using Gd-DTPA or ferric ammonium citrate based paramagnetic agents than when using ferrous sulfate.

Another preferred paramagnetic oil emulsion according to this invention for oral administration comprises about 2 to 3 gms/500 ml dosage, preferably about 3 gms/500 ml, ferric ammonium citrate, about 15 to about 25, preferably about 20 volume percent corn oil, about 20 to about 40, preferably about 30 volume percent ice cream, and about 40 to about 60, preferably about 50 volume percent homogenized milk which results in excellent MRI enhancement by even distribution throughout the small bowel of adult humans.

The specific examples set forth embodiments of the invention in detail which are intended to be illustrative only and are not intended to limit the invention in any way.

EXAMPLE I

An aqueous/oil emulsion paramagnetic contrast agent according to one preferred embodiment of this invention was formulated by mixing the following components for 3 minutes in a blender at high speed to form 500 ml of the paramagnetic oil emulsion:

| Component | Volume Percent |
| --- | --- |
| Homogenized Milk | 38 |
| Melted ice cream (Breyer vanilla, 8% fat) | 30 |
| Corn oil (Mazola) | 20 |
| Geritol ® J.B. Wlliams Co. | 12 |
| 3.38 mg/ml $Fe^{+3}$ (ferric ammonium citrate) | |
| 0.16 mg/ml thiamine | |
| 0.16 mg/ml riboflavin | |
| 3.38 mg/ml niacinamide | |
| 0.13 mg/ml panthenol | |
| 0.03 mg/ml pyridoxine | |
| 1.69 mg/ml methionine | |
| 3.38 mg/ml choline bitartrate | |
| Ethanol 12 volume percent | |

Similar emulsions were formulated varying the amount of Geritol ® from 4 to 20 volume percent, the amounts of corn oil and ice cream being constant and the balance being milk.

EXAMPLE II

Emulsions prepared as described in Example I with varying Geritol ® content from 4 to 12 volume percent were taken orally by human volunteers in the amount of 500 ml uniformly over a two-hour period. The volunteers abstained food and drink for at least four hours prior to ingestion of the emulsions. The volunteers were asked to grade on a scale of 1 to 5: the taste of the emulsion (1 being great and 5 being intolerable), the amount of nausea experienced (1 being none and 5 being severe vomiting), and the amount of abdominal cramps (1 being none and 5 being severe). The volunteers also recorded the duration of discomfort, the timing and frequency of bowel movements and the overall impression of the emulsion ingestion. Results are shown in Table 1:

TABLE 1

| Geritol ® (% v/v) | Taste | Nausea | Abd. Cramps |
| --- | --- | --- | --- |
| 4 | 1 | 1 | 1 |
| 6 | 1 | 1 | 1 |
| 8 | 1 | 1 | 1 |
| 10 | 2 | 1 | 1 |
| 12 | 2 | 1 | 1 |

EXAMPLE III

The volunteers who ingested emulsions referred to in Example II were then imaged using either a 1.5 T Siemens Magnetom MR imager or a General Electric Signa MR imager. Spin echo (SE) pulse sequences with repetition time (TR) of 550 msec and echo time (TE) of 22 msec, and TR of 2000 msec and TE of 90 msec were used. Images were also obtained using gradient echo FLASH pulse sequences with TR of 50 msec, TE of 15 msec and flip angle of 40 degree pulse sequences. The images were then reviewed jointly by two radiologists to evaluate the ability of the contrast agent to opacify the gastrointestinal tract and to enhance delineation of the different abdominal organs. The delineation of the bowel organs were scored on a scale of 1 to 5, 1 being very poor and 5 being excellent, the results being tabulated in Table 2:

degree of opacification are very good to excellent with the various combination of ferric ammonium citrate, Gd-DTPA and the various vegetable oils. Ferrous sulfate produced less enhancement effect as compared to the other two paramagnetic substances tested. Soybean oil emulsion appeared to have a less uniform distribution throughout the bowel. From this study, it is apparent that many different combinations of a paramagnetic agent and an oil can work very well as an enteric MRI contrast agent.

EXAMPLE VI

A paramagnetic oil emulsion was formulated by mix-

TABLE 2

| Geritol ® (% v/v) | % Small Bowel Opacified | Organ Delineation with Best Sequence | Degree of Bowel Enhancement | | |
|---|---|---|---|---|---|
| | | | SE 550/22 | SE 2000/90 | FLASH 50/15/40 |
| 4 | 20 | 2 | 1 | 4 | 3 |
| 6 | 50 | 3 | 2 | 4 | 3 |
| 8 | 70 | 4 | 3 | 4 | 4 |
| 10 | 80 | 4 | 4 | 5 | 5 |
| 12 | >90 | 5 | 5 | 5 | 5 |

EXAMPLE IV

The emulsion prepared as in Example I with 12 percent Geritol ® was taken in 500 ml dosage orally by five human volunteers in the same manner as described in Example II followed by MR imaging in the same manner as described in Example III. The results, using the same scoring system as in Examples II and III is tabulated in Table 3.

ing 150 ml melted ice cream, 250 ml homogenized milk, 100 ml corn oil, and 1.21 grams ferric ammonium citrate powder in a blender at high speed for three minutes. This homogeneous emulsion was taken orally and the subject scanned within 2 hours by MRI as described in Example III. Good delineation of the entire small bowel and good discrimination of the various abdominal organs was observed. The paramagnetic oil emulsion had a more acceptable taste than those in which Geritol ®

TABLE 3

| Volunteer | Taste | Nausea | Abd. Cramps | % Small Bowel Opacified | Organ Delin. with Best Sequence | Degree of Bowel Enhancement | | |
|---|---|---|---|---|---|---|---|---|
| | | | | | | SE 550/22 | SE 2000/90 | FLASH 50/15/40 |
| 1 | 2 | 1 | 1 | >90 | 5 | 5 | 5 | 5 |
| 2 | 2 | 1 | 1 | >90 | 5 | 5 | 5 | 5 |
| 3 | 1 | 1 | 1 | >90 | 5 | 5 | 5 | 5 |
| 4 | 1 | 1 | 1 | 80 | 4 | 5 | 5 | 5 |
| 5 | 2 | 1 | 1 | 80 | 4 | 5 | 5 | 5 |

EXAMPLE V

Paramagnetic agents with various water/oil emulsions were formulated without ice cream and milk for human tests. In each case using Gd-DTPA 1 ml of the indicated paramagnetic agent from a stock solution of 0.5M concentration was used with 100 ml corn oil (20 volume percent) and 400 ml water. For the iron based contrast agent, the iron content in the 500 ml emulsion was 0.2 gms (7 mM). In each composition, the ingestion, imaging and evaluation procedures were the same as set forth in Examples II and III. Each composition was ingested by one person. Results are shown in the following Table 4:

was used as the source of ferric ammonium citrate. When higher dosage (3.0 grams) of ferric ammonium citrate powder was used, the signal intensity enhancement see in the bowel with T1 weighted pulse sequences was more uniform.

EXAMPLE VII

A paramagnetic oil emulsion was prepared in the same manner as described in Example VI except that instead of ferric ammonium citrate as the paramagnetic species, 1 ml of 0.5M aqueous solution of Gadolinium DTPA was used. The Gd-DTPA did not add a metallic taste. In a similar manner, chromium EDTA may be used at concentrations of 0.1 to 10 mM/liter.

TABLE 4

| Paramagnetic Agent | Oil | Taste | Nausea | Abd. Cramps | % Small Bowel Opacified | Organ Delin. with Best Sequence | Degree of Bowel Enhancement | | |
|---|---|---|---|---|---|---|---|---|---|
| | | | | | | | SE 550/22 | SE 2000/90 | FLASH 50/15/40 |
| Ferric Ammonium Citrate | Corn | 3 | 1 | 1 | 80 | 5 | 4 | 5 | 5 |
| Gd-DTPA | Corn | 3 | 1 | 1 | >90 | 5 | 5 | 5 | 5 |
| Gd-DTPA | Peanut | 3 | 1 | 1 | >90 | 5 | 5 | 5 | 5 |
| Gd-DTPA | Soybean | 3 | 1 | 1 | 80 | 5 | 5 | 5 | 5 |
| Ferrous Sulfate | Corn | 4 | 1 | 1 | 80 | 4 | 3 | 5 | 3 |

The above table shows that without the ice cream and milk the generic combinations tasted fairly bad. However, their distribution throughout the bowel and

EXAMPLE VIII (COMPARISON)

An emulsion was made with different amount of corn oil and ice cream indicated in Table 5 with the balance being homogenized milk. These were tasted by human volunteers with the noted effects rated in the same manner as described in Example II followed in indicated cases by MR imaging in the same manner as described in Example III.

TABLE 5

| Corn Oil (% v/v) | Ice Cream (% v/v) | Taste | Nausea | Abd. Cramps | % Small Bowel Opacified | Organ Delin. with Best Sequence | Degree of Bowel Enhancement | | |
|---|---|---|---|---|---|---|---|---|---|
| | | | | | | | SE 550/22 | SE 2000/90 | FLASH 50/15/40 |
| 15 | 0 | 3 | 1 | 1 | 60 | 3 | 1 | 4 | 3 |
| 20 | 0 | 3 | 1 | 1 | 70 | 3 | 2 | 4 | 3 |
| 25 | 0 | 4 | 1 | 1 | 70 | 4 | 2 | 4 | 3 |
| 10 | 10–30 | 1 | | | | | | | |
| 20 | 10–30 | 1 | | | | | | | |
| 30 | 10–30 | 2 | | | | | | | |
| 40 | 10–30 | 2 | | | | | | | |

Table 5 shows that the MRI enhancement effect of the oil emulsion, without the paramagnetic agent is inadequate, especially with the T1 weighted SE sequence. Further, Table 5 shows that the taste is unacceptable without the inclusion of ice cream.

EXAMPLE IX

Magnetic resonance signal to noise ratios were obtained using T-1 weighted sequence (SE 500/20) as a function of ferric ammonium citrate and corn oil content in various compositions having 30 volume percent ice cream and the balance milk in test tubes. Compared to 0 percent corn oil there was an initial increase in signal to noise ratios from about 200 to about 300 with 20 volume percent corn oil emulsion with no ferric ammonium citrate present. Upon addition of ferric ammonium citrate, the signal to noise ratio in corn oil concentrations of 0 to 20 volume percent peaked at 600 to 700 with about 1 gram per liter ferric ammonium citrate and decreased at higher ferric ammonium citrate concentrations due to T-2 shortening effect. It is observed that the signal intensity enhancement caused by ferric ammonium citrate is much greater than caused by the oil alone.

While in the foregoing specification this invention has been described in relation to certain preferred embodiments thereof, and many details have been set forth for purpose of illustration it will be apparent to those skilled in the art that th invention is susceptible to additional embodiments and that certain of the details described herein can be varied considerably without departing from the basic principles of the invention.

We claim:

1. A paramagnetic oil emulsion comprising: about 5 to about 30 volume percent oil and about 70 to about 95 volume percent aqueous medium, said paramagnetic oil emulsion having dissolved therein a magnetic resonance imaging contrast effective and less than a toxic amount of at least one paramagnetic agent.

2. A paramagnetic oil emulsion according to claim 1 wherein said oil comprises predominately vegetable oil.

3. A paramagnetic oil emulsion according to claim 1 wherein said oil is vegetable oil selected from the group consisting of corn, olive, peanut, soybean, and mixtures of such oils.

4. A paramagnetic oil emulsion according to claim 1 wherein said aqueous medium comprises milk and ice cream.

5. A paramagnetic oil emulsion according to claim 1 wherein said aqueous medium comprises about 20 to about 50 volume percent milk and about 20 to about 40 volume percent ice cream, based upon the total said oil emulsion.

6. A paramagnetic oil emulsion according to claim 1 wherein said emulsion comprises about 15 to about 25 volume percent said oil and about 75 to about 85 volume percent said aqueous paramagnetic carrier.

7. A paramagnetic oil emulsion according to claim 1 wherein said wherein oil comprises predominately vegetable oil and said aqueous paramagnetic carrier comprises milk and ice cream.

8. A paramagnetic oil emulsion according to claim 1 wherein said emulsion comprises about 15 to about 25 volume percent vegetable oil selected from the group consisting of corn, olive, peanut, soybean, and mixtures of such oils.

9. A paramagnetic oil emulsion according to claim 1 wherein said paramagnetic agent comprises an iron based material.

10. A paramagnetic oil emulsion according to claim 9 wherein said iron based material is selected from the group consisting of ferric ammonium citrate, iron sulfate and mixtures thereof.

11. A paramagnetic oil emulsion according to claim 1 wherein said paramagnetic agent is water soluble ferric ammonium citrate.

12. A paramagnetic oil emulsion according to claim 11 wherein said ferric ammonium citrate is present in a dosage amount of about 0.75 to about 3 grams.

13. A paramagnetic oil emulsion according to claim 1 wherein said oil comprises predominately vegetable oil, said paramagnetic agent is ferric ammonium citrate, and said aqueous medium comprises about 20 to about 50 volume percent milk and about 20 to about 40 volume percent ice cream, based upon the total said oil emulsion.

14. A paramagnetic oil emulsion according to claim 1 wherein said oil comprises corn oil in an amount of about 15 to 25 volume percent, said aqueous medium comprises about 40 to about 60 volume percent milk and about 20 to about 40 volume percent ice cream, based upon the total said oil emulsion, and said paramagnetic agent is ferric ammonium citrate present in a dosage amount of about 0.75 to about 3 grams.

15. A paramagnetic oil emulsion according to claim 1 additionally comprising a thickening agent in an amount of about 2 to about 8 percent of said emulsion.

16. A paramagnetic oil emulsion according to claim 1 wherein said paramagnetic agent is dissolved in said oil.

17. A paramagnetic oil emulsion for human oral administration, said emulsion comprising: about 5 to about 30 volume percent oil and about 70 to about 95 volume percent aqueous medium, said paramagnetic oil emulsion having dissolved therein a flavor enhancement agent and a magnetic resonance image contrast effective and less than a toxic amount of at least one paramagnetic agent.

18. A paramagnetic oil emulsion according to claim 17 wherein said oil comprises predominately vegetable oil.

19. A paramagnetic oil emulsion according to claim 17 wherein said oil is vegetable oil selected from the group consisting of corn, olive, peanut, soybean, and mixtures of such oils.

20. A paramagnetic oil emulsion according to claim 17 wherein said aqueous medium comprises about 20 to about 50 volume percent milk and about 20 to about 40 volume percent ice cream, based upon the total said oil emulsion.

21. A paramagnetic oil emulsion according to claim 17 wherein said emulsion comprises about 15 to about 25 volume percent said oil, about 75 to about 85 volume percent said aqueous medium and said paramagnetic agent is ferric ammonium citrate in an amount of about 0.75 to about 3 grams per dose.

22. A paramagnetic oil emulsion according to claim 17 wherein said paramagnetic agent is dissolved in said oil.

23. A paramagnetic oil emulsion according to claim 17 wherein said flavor enhancement agent is dissolved in said oil.

24. In a method of imaging a body cavity of a patient by magnetic resonance after enteric administration to the patient of a magnetic resonance contrast medium, the improvement comprising: administering enterically a paramagnetic oil emulsion, said emulsion comprising: about 5 to about 30 volume percent oil and about 70 to about 95 volume percent aqueous medium, said paramagnetic oil emulsion having dissolved therein a magnetic resonance image contrast effective and less than a toxic amount of at least one paramagnetic agent.

25. In a method of imaging according to claim 24 wherein said oil comprises predominately vegetable oil.

26. In a method of imaging according to claim 24 wherein said oil is vegetable oil selected from the group consisting of corn, olive, peanut, soybean, and mixtures of such oils.

27. In a method of imaging according to claim 24 wherein said aqueous medium comprises milk and ice cream.

28. In a method of imaging according to claim 24 wherein said aqueous medium comprises about 20 to about 60 volume percent milk and about 20 to about 40 volume percent ice cream, based upon the total said oil emulsion.

29. In a method of imaging according to claim 24 wherein said emulsion comprises about 15 to about 25 volume percent said oil and about 75 to about 85 volume percent said aqueous medium.

30. In a method of imaging according to claim 24 wherein said wherein said oil comprises predominately vegetable oil and said aqueous medium comprises milk and ice cream.

31. In a method of imaging according to claim 24 wherein said emulsion comprises about 15 to about 25 volume percent vegetable oil selected from the group consisting of corn, olive, peanut, soybean, and mixtures of such oils.

32. In a method of imaging according to claim 24 wherein said paramagnetic agent comprises an iron based material.

33. In a method of imaging according to claim 32 wherein said paramagnetic agent is selected from the group consisting of ferric ammonium citrate, iron sulfate and mixtures thereof.

34. In a method of imaging according to claim 24 wherein said paramagnetic agent is ferric ammonium citrate in a dosage of about 0.75 to about 3 grams.

35. In a method of imaging according to claim 24 wherein said oil comprises predominately vegetable oil, said paramagnetic agent is ferric ammonium citrate, and said aqueous medium comprises about 20 to about 50 volume percent milk and about 20 to about 40 volume percent ice cream, based upon the total said oil emulsion.

36. In a method of imaging according to claim 24 wherein said oil comprises corn oil in an amount of about 15 to 25 volume percent, said aqueous medium comprises about 20 to about 50 volume percent milk and about 20 to about 40 volume percent ice cream, based upon the total said oil emulsion, and said paramagnetic agent is ferric ammonium citrate in a dosage amount of about 0.75 to about 3 grams.

37. In a method of imaging according to claim 24 wherein said body cavity comprises the small bowel.

38. In a method of imaging according to claim 24 wherein said body cavity comprises the distal small bowel.

39. A method for obtaining an in vivo magnetic resonance image of the gastrointestinal tract of a human subject comprising: administering enterically to said subject a paramagnetic oil emulsion comprising about 5 to about 30 volume percent oil and about 70 to about 95 volume percent aqueous medium, said paramagnetic oil emulsion having dissolved therein a magnetic resonance image contrast effective and less than a toxic amount of at least one paramagnetic agent; and obtaining the magnetic resonance image after a time period sufficient to allow said paramagnetic oil emulsion to pass to the desired portion of the gastrointestinal tract.

40. A method for obtaining an in vivo magnetic resonance image according to claim 39 wherein said paramagnetic oil emulsion has dissolved therein a flavor enhancement agent and is administered orally.

41. A method for obtaining an in vivo magnetic resonance image according to claim 40 wherein said oral administration is given in multiple doses from about 90 minutes prior to immediately prior to said scanning.

42. A method for obtaining an in vivo magnetic resonance image according to claim 39 wherein said paramagnetic oil emulsion is administered rectally.

43. A method for obtaining an in vivo magnetic resonance image according to claim 39 herein said aqueous medium comprises about 20 to about 60 volume percent milk and about 20 to about 40 volume percent ice cream, based upon the total said oil emulsion.

44. A method for obtaining an in vivo magnetic resonance image according to claim 39 wherein said oil comprises predominately vegetable oil.

45. A method for obtaining an in vivo magnetic resonance image according to claim 39 wherein said oil is vegetable oil selected from the group consisting of corn, olive, peanut, soybean, and mixtures of such oils.

46. A method for obtaining an in vivo magnetic resonance image according to claim 39 wherein said emulsion comprises about 15 to about 25 volume percent said oil, about 75 to about 85 volume percent said aqueous medium, and said paramagnetic agent is present in a dosage amount of about 0.75 to about 3 grams.

47. A method for obtaining an in vivo magnetic resonance image according to claim 39 wherein said desired portion of the gastrointestinal tract comprises the small bowel.

48. A method for obtaining an in vivo magnetic resonance image according to claim 39 wherein said desired portion of the gastrointestinal tranct comprises the distal small bowel.

* * * * *